United States Patent [19]

Schnur

[11] 4,193,996
[45] Mar. 18, 1980

[54] SPIRO-QUINOLONE HYDANTOINS

[75] Inventor: Rodney C. Schnur, Noank, Conn.

[73] Assignee: Pfizer Inc., New York, N.Y.

[21] Appl. No.: 26,990

[22] Filed: Apr. 4, 1979

[51] Int. Cl.$^2$ .................... C07D 471/10; A61K 31/47
[52] U.S. Cl. ...................................... 424/256; 546/18; 546/15
[58] Field of Search ..................... 546/15, 18; 424/256

[56] References Cited
U.S. PATENT DOCUMENTS 4,117,230  9/1978  Sarges .................................. 548/309

*Primary Examiner*—Alan L. Rotman
*Assistant Examiner*—Robert T. Bond
*Attorney, Agent, or Firm*—Francis X. Murphy; Charles J. Knuth; Peter C. Richardson

[57] ABSTRACT

Novel spiro-quinolone hydantoin derivatives useful as aldose reductase inhibitors and as therapeutic agents for the treatment of chronic diabetic complications are disclosed. Pharmaceutical compositions containing the novel compounds and a method of treating chronic diabetic complications are also disclosed. Preferred compounds include spiro[2,3-dihydro-1H,5H-benzo[ij]-quinolizin[1,4']imidazolidin]-2',5,5=-trione and 10-chloro-spiro[2,3-dihydro-1H,5H-benzo[ij]-quinolizin[1,4']imidazolidin]-2',5,5'-trione.

10 Claims, No Drawings

SPIRO-QUINOLONE HYDANTOINS

BACKGROUND OF THE INVENTION

This invention relates to novel spiro-quinolone hydantoin derivatives useful in the treatment of certain chronic complications arising from diabetes mellitus, such as diabetic cataracts, retinopathy and neuropathy, to pharmaceutical compositions containing such compounds and to a method of using the compounds.

In the past, various attempts have been made to obtain new and more effective oral anti-diabetic agents. Generally, these efforts have involved synthesis of new organic compounds, particular sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. Such aldose reductase inhibitors function by inhibiting the activity of the enzyme aldose reductase, which is primarily responsible for regulating the reduction of aldoses such as glucose and galactose to the corresponding polyols, such as sorbitol and galacticol, in humans and other animals. In this way, unwanted accumulations of galacticol in the lens of galactosemic subjects and of sorbitol in the lens, peripheral nervous cord and kidney of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel spiro-quinolone hydantoins of the formula

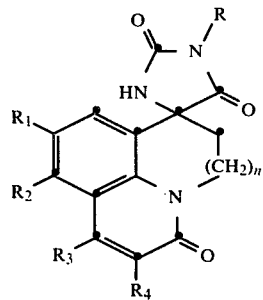

and the pharmaceutically acceptable addition salts thereof, wherein n is one or two; R, $R_3$ and $R_4$ are each hydrogen; and $R_1$ and $R_2$, are each selected from the group consisting of hydrogen, chloro, bromo, fluoro, alkyl of 1 to 3 carbon atoms and alkoxy of 1 to 3 carbon atoms. Preferably $R_1$, and $R_2$, are each selected from hydrogen, chloro and bromo.

A preferred group of compounds is that wherein n is one, especially where $R_1$, and $R_2$, are each selected from hydrogen, chloro and bromo. Preferred compounds of this group are those wherein $R_1$, and $R_2$ are each hydrogen and wherein $R_1$ is chloro and $R_2$ is hydrogen.

Additionally compounds wherein R is alkyl of 1 to 4 carbon atoms, benzyl or substituted benzyl, or wherein $R_3$ and $R_4$ are chloro, bromo, fluoro, alkyl of 1 to 3 carbon atoms or alkoxy of 1 to 3 carbon atoms are, for the purposes of this invention, equivalent to compounds having R, $R_3$ and $R_4$ groups as defined hereinabove and such compounds are within the scope of this invention.

The present invention further comprises a novel method for the treatment of a diabetic host to prevent or alleviate diabetes-associated complications, such as cataracts, neuropathy or retinopathy which method comprises administering to the host an effective amount of a compound of formula I. Preferred compounds employed in this method of treatment are the preferred compounds of formula I as described hereinabove.

Also embraced by the present invention are pharmaceutical compositions comprising a pharmaceutically acceptable carrier and a compound of formula I in an amount effective to prevent or alleviate diabetes-associated complications, such as cataracts, neuropathy or retinopathy. Preferred compounds for use in such pharmaceutical compositions are those preferred compounds of formulae I as described hereinabove.

DETAILED DESCRIPTION OF THE INVENTION

The novel compounds of formula I are prepared from appropriately substituted ketones of the formula

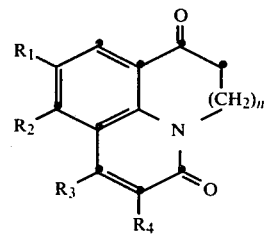

The ketone starting materials of formula II are prepared from the appropriately substituted 3[1(2-oxo-1-,2-dihydroquinolin)]-propionitrile, for compounds wherein n is one, or the corresponding -n-butyronitrile, for compounds wherein n is two. The nitriles are prepared by the method described by Bates in J. Chem. Soc. 1954, 1153. Thus, for example, an appropriately substituted 1,2-dihydroquinolin-2-one is reacted with acrylonitrile in an inert organic solvent such as N,N-dimethylformamide at a temperature between about 20° C. and 100° C.

The nitriles are first hydrolyzed to the corresponding 3[1-(2-oxo-1,2-dihydroquinolin)]propanoic acid or 4-[1-(2-oxo-1,2-dihydroquinolin)]-n-butyric acid by heating in acid, such as hydrochloric acid, formic acid or the like, preferably at reflux temperature. The acids produced are then heated in the presence of a strong acid such as polyphosphoric acid, sulfuric acid, p-toluene sulfuric acid or the like at a temperature of about 75° C. to 150° C. to form the ketones of formula II. The reaction may also be effected by reaction of the 3-substituted-propanoic acid or 4-substituted-n-butyric acid with thionyl chloride at a temperature of about 10° C. to 40° C. to form the corresponding acid chloride, followed by heating in the presence of a Lewis acid, such as aluminum chloride, in an inert organic solvent such as nitrobenzene, nitromethane and the like.

The 3-[1-(2-oxo-1,2-dihydroquinolin)]propanoic acid or 4-[1-(2-oxo-1,2-dihydroquinolin)]-n-butyric acid intermediates may also be formed by reaction of a 3-halopropionic acid or 4-halo-n-butyric acid, preferably chloro- or bromo- substituted, with an alkali metal salt of 1,2-dihydroquinol-2-one in the presence of a base such as an alkali metal hydroxide or hydroxide in an inert organic solvent such as dimethylformamide, dimethylacetamide and the like at a temperature of about 50° to 150° C. The acids are then converted to the ketone starting materials of formula II as described above.

The ketone of formula II is then condensed with an alkali metal cyanide, such as sodium cyanide or potassium cyanide, and ammonium carbonate to form the desired spiro-quinolone hydantoin of formula I. The reaction is generally conducted in an inert polar organic reaction solvent in which both the reactants and reagents are mutually miscible. Preferred organic solvents include, but are not limited to cyclic ethers such as dioxane and tetrahydrofuran, lower alkylene glycols such as ethylene glycol and trimethylene glycol, lower alkanols such as methanol, ethanol and isoproponol and N,N-dialkyl-alkanoamides such as N,N-dimethylformamide, N,N-diethylformamide and N,N-dimethylacetamide. In general, the reaction is conducted at a temperature of between about 50° C. and about 150° C., preferably about 90° C. to 130° C., for a period of about 2 hours to about 4 days, depending on the temperature employed. Although the proportions of reactants and reagents employed in the reaction can vary to some extent, it is preferable to employ at least a slight molar excess of the alkali metal cyanide reagent with respect to the ketone of formula II in order to obtain the maximum yield. Upon completion of the reaction, the desired product is readily isolated by conventional means, for example by first diluting the reaction mixture with water and then cooling the resultant aqueous solution to room temperature, followed by acidification to afford the desired spiro-quinolone hydantoin in the form of a readily recoverable precipitate.

If desired, compounds of formula I wherein any of $R_1$, $R_2$, $R_3$ or $R_4$ are hydrogen may be converted by known reaction methods to compounds having other substituent groups, within the scope of the invention, as defined previously. Thus, for example, such compounds of formula I may be directly halogenated by reaction with a halogen, especially chlorine or bromine, in the presence a Lewis acid catalyst, for example, aluminum chloride or ferric chloride, the reaction being generally conducted in an inert organic solvent, such as dimethylformamide or the like, at a temperature between about $-50°$ C. and 0° C.

Production of compounds of formula I wherein R is alkyl or benzyl is effected by further reacting those compounds where R is hydrogen to introduce the desired substituent, using alkylation reactions well-known in the art. For example, the compounds of formula I wherein R is hydrogen are reacted with an appropriate alkyl halide or benzyl halide, preferably the chloride or bromide, in the presence of a base such as an alkali metal hydroxide, alkoxide or carbonate or a trialkylamine, such as triethylamine. The reaction is generally conducted at a temperature between about 0° C. and 140° C. in a reaction inert solvent such as acetone, a lower alkyl alcohol, dimethyl formamide, an ether such as diethyl ether, tetrahydrofuran, dioxane and the like.

Pharmaceutically acceptable salts can be readily prepared from compounds of formula I wherein R is hydrogen by conventional methods. Thus, these salts may be readily prepared by treating such spiro-quinolone hydantoins with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and subsequently evaporating the solution to dryness. Suitable pharmaceutically acceptable cations for this purpose include, but are not limited to, potassium, sodium, ammonium, calcium and magnesium.

The novel spiro-quinolone hydantoins of formula I are useful as aldose reductase inhibitors, and as such are of therapeutic value in the treatment of chronic complications of diabetes, such as cataracts, retinopathy and neuropathy. As used in the claims and specification hereof, treatment is meant to include both prevention or alleviation of such conditions. The compounds may be administered to a subject in need of treatment by a variety of conventional routes of administration, including orally, parenterally and topically. In general, these compounds will be administered at dosages between about 1 and 250 mg/kg body weight of the subject to be treated per day. However, some variation in dosage will necessarily occur depending on the condition of the subject being treated and the person responsible for administration will, in any event, determine the appropriate dose for the individual subject.

The compounds may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes or oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel spiro-quinolone hydantoins of formula I in sesame or peanut oil or in aqueous propylene glycol may be employed, as well as sterile aqueous solutions of the corresponding water-soluble alkali metal or alkaline earth metal salts previously described. Such aqueous solutions should be suitably buffered if necessary and the liquid diluent first rendered isotonic with sufficient saline or glucose. These particular aqueous solutions are especially suitable for intraveneous, intramuscular, subcutaneous and intraperitoneal administration. In this connection, the sterile aqueous media employed are all readily available by standard techniques known to those skilled in the art. Additionally, it is also possible to administer the spiro-quinolone hydantoin derivatives topically, by use of an appropriate ophthalmic solution which may then be administered drop-wise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats.

The present invention is illustrated by the following examples. It will be understood, however, that the invention is not limited to the specific details of these examples.

EXAMPLE 1

3[1-(2-oxo-1,2-dihydroquinolin)]-propanoic acid

3[1-(2-oxo-1,2-dihydroquinolin)]propionitrile (10.0 g, 50.0 mol) prepared by the method of Bates, J. Chem. Soc.; 1954, 1153, was refluxed for 0.75 hours in a mixture of 25 ml 98% formic acid and 25 ml concentrated hydrochloric acid. The mixture was poured onto ice with stirring. The precipitated product was collected by filtration washed with water and dried in vacuo at 60° C.; 10.74 g (98%), mp 195°–198° C.

EXAMPLE 2

2,3-Dihydro-1H, 5-benzo[ij]quinolizin-1,5-dione

A mixture of 50 ml polyphosphoric acid (Stauffer) and 3-[1-(2-oxo-1,2-dihydroquinolin)]-propanoic acid (5.0 g, 23.0 mmol) was heated to 140° C. with an oil bath for 2 hours. The cooled reaction mixture was poured into 300 ml ice water. The aqueous solution was extracted with 300 ml ethyl acetate. The organic phase was washed with brine and saturated sodium bicarbonate over magnesium sulfate dried, filtered, and evaporated in vacuo to a solid; 1.95 g (42%) mp 185°–187.5° C. Recrystallization from ethanol afforded orange needles; 1.40 g, mp 188°–190.5° C.

EXAMPLE 3

Spiro[2,3-dihydro-1H, 5H-benzo[ij]quinolizin [1,4'] imidazolidin]-2', 5, 4'-trione A solution of potassium cyanide (0.412 g 6.33 mmol) and ammonium carbonate (1.36 g, 14.1 mmole) dissolved in 7 ml water was added to a solution of 2,3 dihydro-1H, 5H-benzo[ij]quinolizin-1,5-dione (0.700 g, 3.52 mmol) in 7 ml ethanol and the resulting mixture heated at 60° C. overnight. The reaction mixture was diluted with 25 ml water and boiled for 10 minutes. After cooling and basification to pH 11 with 6 N sodium hydroxide and homogeneous solution was washed with chloroform, (2×100 ml). After acidification of the aqueous phase to pH 1 with sulfuric acid a precipitate formed which was collected, washed with water and dried in vacuo at 54° C.; 0.760 g (80%), mp 290°–292° C. (dec).

EXAMPLE 4

10-Chloro-spiro[2,3-dihydro-1H, 5H-benzo[ij]quinolizin[1,4']imidazolidin]-2', 5, 5'-trione The compound of Example 3 (0.539 g, 2.0 mmol) was dissolved in 4 ml of NN-dimethylformamide containing chlorine gas (0.142 g, 2.0 mmol) was added dropwise. The mixture was kept at $-30°$ C. to $-40°$ C. for two hours then allowed to warm to room temperature overnight. 50 ml water was added and a trace residue filtered. The filtrate was evaporated in vacuo to a residue which was triturated with ether. The solid was recrystallized from ethanol; 0.300 g (50%) mp 200°–210° C. (dec). This material was column chromatographed on silica gel by elution with chloroform: methanol: acetic acid (90:5:5) to give a pure sample of the title compound, mp 199°–205° C. (dec).

EXAMPLE 5

Following the procedure of Example 1 to 3 the following compounds of formula I are prepared, wherein R, $R_3$ and $R_4$ are all hydrogen and n is one:

| $R_1$ | $R_2$ |
|---|---|
| Methyl | Hydrogen |
| Hydrogen | Chloro |
| Hydrogen | Methyl |

Suitable starting materials are disclosed by Effenberger and Hartmann, Chem. Ber. 102, 3260 (1969).

EXAMPLE 6

Sprio[1,2,3,4-tetrahydro-azepino[3,2,1-ij]quinolizin [1,4']imidazolidin]-2',5',6-trione The procedures of Examples 1, 2, and 3 may be repeated using as starting material 4[1-(2-oxo-1,2-dihydroquinolin]-n-butyronitrle to form the title compound.

EXAMPLE 7

The compounds of Examples 3 and 4 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-6}M$ are expressed as percent inhibition of enzyme activity.

| Compound of | % Inhibition at $10^{-6}m$ |
|---|---|
| Example 3 | 86 |
| Example 4 | 94 |

EXAMPLE 8

The compounds of Examples 3 and 4 were tested for their ability to reduce or inhibit sorbitol accumulation in the sciatic nerve of streptozotocinized (i.e. diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of streptozotocin. The results obtained in this manner are presented below in terms of percent inhibition (%) afforded by the test compound as compared to the case where no compound was administered (i.e. the untreated animal, where sorbitol levels normally rise from approximately 50—100 mM/g. tissue to as high as 400 mM/g. tissue in the 27-hour test period):

| Compound of | % Inhibition at 1.5 mg/kg |
|---|---|
| Example 3 | 27 |
| Example 4 | 32 |

I claim:

1. A compound of the formula

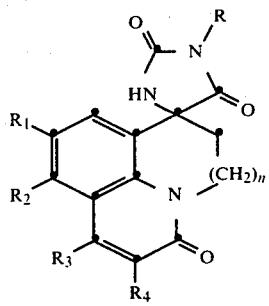

and the pharmaceutically acceptable addition salts thereof, wherein n is one or two; R, $R_3$ and $R_4$ are each hydrogen; and $R_1$, and $R_2$ are each selected from the group consisting of hydrogen, chloro, bromo, fluoro, alkyl of 1 to 3 carbon atoms and alkoxy of 1 to 3 carbon atoms.

2. A compound of claim 1 wherein n is one.
3. A compound of claim 2 wherein $R_1$ and $R_2$ are each selected from hydrogen, chloro and bromo.
4. A compound of claim 3 wherein $R_1$ and $R_2$ are each hydrogen.
5. A compound of claim 3 wherein $R_1$ is chloro and $R_2$ is hydrogen.
6. A pharmaceutical composition comprising a pharmaceutically acceptable carrier and a compound of claim 1 in an amount effective for the treatment of diabetic cataracts, neuropathy or retinopathy.
7. A pharmaceutical composition of claim 6 wherein n is one.
8. A pharmaceutical composition of claim 7 wherein $R_1$ and $R_2$ are each hydrogen.
9. A pharmaceutical composition of claim 8 wherein $R_1$ is chloro and $R_2$ is hydrogen.
10. A method for treating a diabetic host for diabetic cataracts, neuropathy or retinopathy which comprises administering to said host an effective amount of a compound of claim 1.

* * * * *